(12) United States Patent
Pitacco

(10) Patent No.: US 11,013,633 B2
(45) Date of Patent: May 25, 2021

(54) MENSTRUAL CUP AND EXTRACTOR SYSTEM

(71) Applicant: Athena Holding Srl, Turin (IT)

(72) Inventor: Paolo Pitacco, Turin (IT)

(73) Assignee: Athena Holding Srl, Turin (IT)

( * ) Notice: Subject to any disclaimer, the term of this patent is extended or adjusted under 35 U.S.C. 154(b) by 239 days.

(21) Appl. No.: 16/216,045

(22) Filed: Dec. 11, 2018

(65) Prior Publication Data

US 2020/0179157 A1 Jun. 11, 2020

(51) Int. Cl.
*A61F 5/455* (2006.01)
*A61F 5/44* (2006.01)

(52) U.S. Cl.
CPC .......... *A61F 5/4553* (2013.01); *A61F 5/4404* (2013.01)

(58) Field of Classification Search
CPC .......... A61F 5/455; A61F 5/4553; A61F 6/12
See application file for complete search history.

(56) References Cited

FOREIGN PATENT DOCUMENTS

| CN | 103705332 B | 6/2017 |
|---|---|---|
| KR | 20180114500 A | 10/2018 |
| WO | WO 2014015975 A1 | 1/2014 |

*Primary Examiner* — Ariana Zimbouski
(74) *Attorney, Agent, or Firm* — Leason Ellis LLP

(57) ABSTRACT

A menstrual device includes a cup and an extractor. Within the cup is a hollow projection having a channel which communicates with a guide. A blunt tip of the extractor is guided by the guide and received in the hollow projection. The extractor further includes a helical section proximal to the blunt tip which is configured to securely engage the cup from within the hollow projection. A handle portion of the extractor facilitates advancement of the blunt tip and extraction of the extractor together with the cup, once the two are engaged with each other. In a specific embodiment, the guide has a free end with a larger opening than an opposite end which is adjacent the cup, to better guide the blunt tip into the hollow projection. The hollow projection can have a frictional surface or threading for the engagement to the helical portion of the extractor.

16 Claims, 5 Drawing Sheets

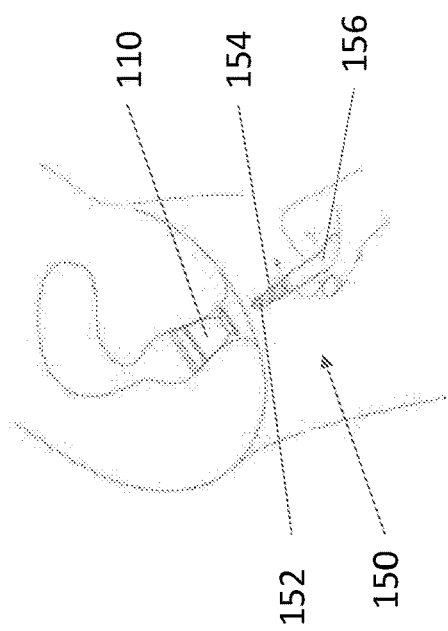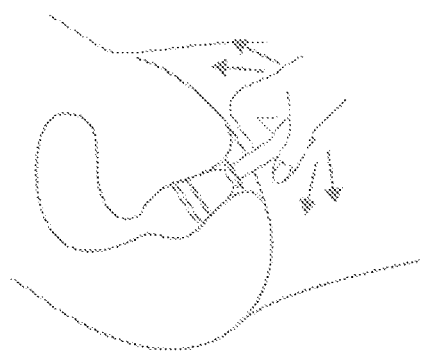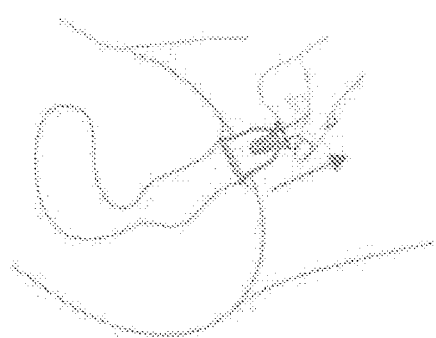
FIG. 5

MENSTRUAL CUP AND EXTRACTOR SYSTEM

FIELD OF THE INVENTION

The present invention relates to feminine hygiene products, and, more particularly to reusable menstrual cups and complementary extractors which cooperate with one another to provide a system for use by persons during multiple menstrual cycles.

BACKGROUND OF THE INVENTION

Nowadays, tampons are widely used by women during their respective menstrual cycles throughout the world. Compared to pads, tampons are smaller in size, users do not have a "wet" feeling, and are better able to more comfortably enjoy activity during their menstrual cycles without fear of soiling. However, usage of tampons can lead to toxic shock syndrome, which is a variety of a staph infection, and this risk is heightened when super absorbent tampons are used. In addition, tampons are not reusable, and therefore they are not environmentally friendly. On the other hand, menstrual cups can contain flow during menstrual cycles and yet are reusable. As such, they provide certain advantages while avoiding the foregoing risks and negative impact of using disposable feminine products.

Currently, most menstrual cups on the market require fingers to be used for both placement and extraction. One known, commercially available menstrual cup sold under the AmyCup brand of the present assignee, includes an extractor. The construction of that cup and extractor has limitations because the extractor is not isolated from sensitive body tissue while in use. New constructions are needed in the art to address such problems, and the present invention addresses these and other needs in the art.

SUMMARY OF THE INVENTION

The present invention is about an improved menstrual device. The menstrual device includes a cup, a guide attached to the cup, a hollow projection extending within the interior of the cup and an extractor. When in use, the extractor is isolated from sensitive body tissue. The cup is connected with the hollow projection at the bottom end, with the guide attached to the bottom of the cup. The extractor is inserted into a channel inside the cup through the lead of a guide. The extractor has helical section, and the helical section frictionally engages the channel in response to rotation of the extractor. The extractor has blunt tip, so that even if inserted in a completely wrong direction and the tip reached human tissue, the blunt tip would not hurt human body.

In a broad aspect, the present invention concerns improvements to menstrual devices. According to one aspect, the menstrual device comprises a cup and an extractor. The cup has a top, a bottom, a shaped exterior, and an interior. The extractor has a blunt tip, a shaped handle, and a helical section extending between the tip and the handle portion. The cup has a guide attached to it. The guide has an opposite, free end and defines a first opening into the bottom of the cup and a second opening at the free end. A hollow projection extends within the interior of the cup and has a channel in communication with the first opening and the second opening. The tip of the extractor is sized and shaped to be received and secured within the hollow projection. The cup and extractor cooperate to interlock in a manner that isolates the engagement from sensitive body tissue. Moreover, the blunt tip of the extractor can be advanced toward engagement with the cup at a variety of angles without hurting tissue.

According to a further aspect, the second opening at the free end of the guide is larger than the opening at the first end of the cup in order to facilitate receipt and securement of the tip and helical section within the hollow projection.

According to a still further aspect, at least the channel of the hollow projection comprises a material that frictionally engages the helical section of the extractor, optionally in response to rotation of the extractor.

According to a further aspect, at least the channel of the hollow projection further comprises threading for threadedly engaging the helical section of the extractor. The threading is within the hollow projection, and in certain arrangements the threading can terminate before the first opening in the guide.

According to a still further aspect, the guide defines a funnel to mechanically direct the blunt tip and the helical section into the hollow projection. Optionally, the funnel can have a conical shape.

In certain implementations, the shaped exterior of the cup comprises a cylinder, a convex, a concave, or a tapered exterior. In the same or further implementations, the cup can include a reinforcing rim which projects from the shaped exterior at a location between the top and the bottom of the cup. In the same or further implementations, the handle portion of the extractor comprises a cylinder, a convex, a concave, or a tapered exterior.

These and other features, aspects and advantages will be apparent from the following discussion of certain embodiments of the invention which is described in conjunction with the accompanying drawing figures.

BRIEF DESCRIPTION OF THE DRAWING FIGURES

FIG. 5A illustrates a first step in the process of removing the cup from a person using the extractor.

FIG. 5B illustrates a second step in the process of removing the cup from a person using the extractor.

FIG. 5C illustrates a third in the process of removing the cup from a person using the extractor.

DETAILED DESCRIPTION OF CERTAIN EMBODIMENTS OF THE INVENTION

By way of overview and introduction, the present application discloses a menstrual device which is configured to reduce, if not eliminate, the risk of hurting human tissue when being removed from the body. In one or more implementations, a menstrual cup, referred to more generally herein as "cup," is inserted into a human body to collect and hold blood during the time of the month that a woman is having her period. Generally, the cup has a top, a bottom, a shaped exterior, and an interior. The menstrual device also includes an extractor which is provided for assisting in removal of the menstrual cup from the human body. As described further below, the extractor can be configured to have a blunt tip, a shaped handle, and a helical section extending between the tip and the handle portion. A hollow projection extends within the interior of the cup. The channel of hollow projection comprises a material that either frictionally engages the helical section of the extractor, or can maintain a shape suitable for enabling engagement of the extractor with the cup. A guide extends from the cup and is provided to direct the tip of the extractor into the hollow projection in order to better enable engagement between the extractor and the cup.

Figure 1B:
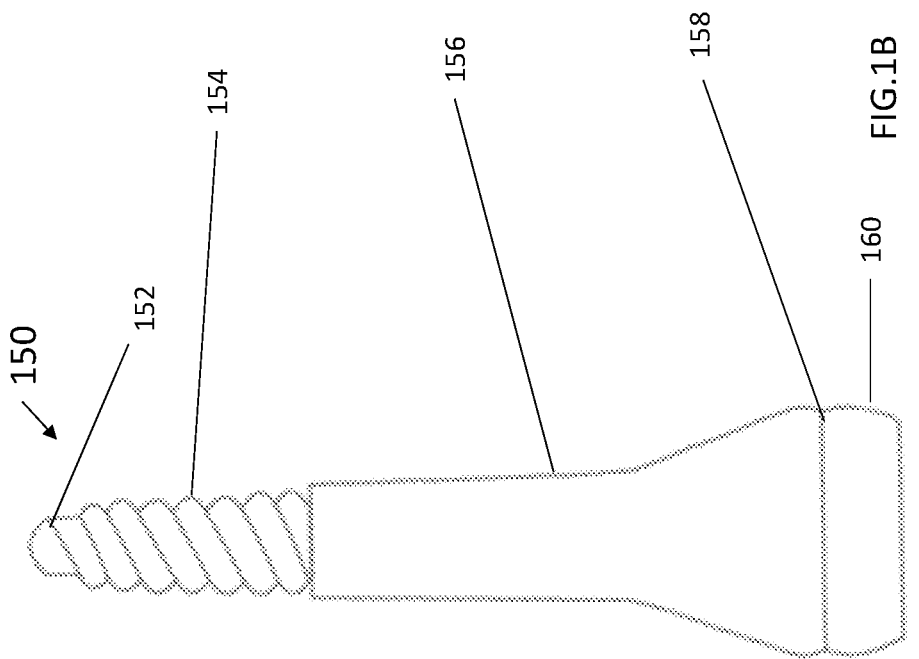
FIG. 1B illustrates an extractor that comprises a second part of the embodiment of FIG. 1A.
Figure 1A:
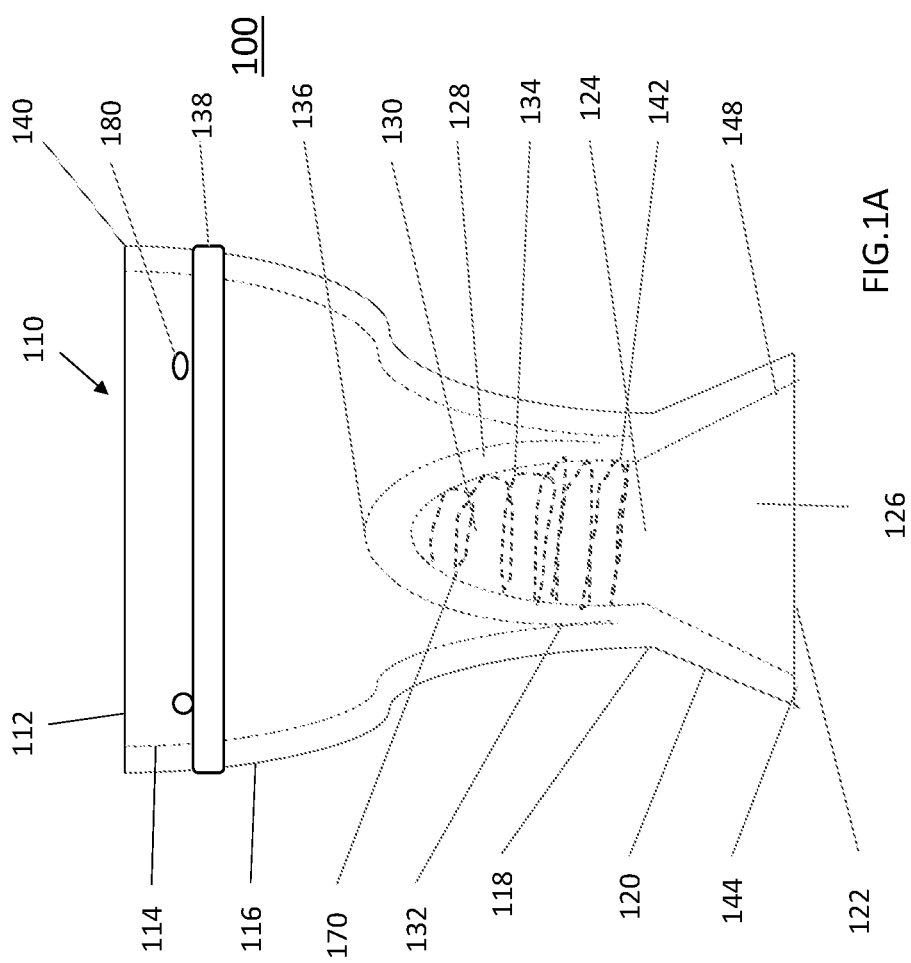
FIG. 1A illustrates a cup that can comprise part of an embodiment of the menstrual device, shown partially in section.

With reference now to FIGS. 1A and 1B, a menstrual device 100 comprises a cup 110 and an extractor 150. The cup 110 includes a guide 120 attached to cup 110 at the bottom. The guide 120 can be integrally formed together with the cup, such as by a molding process. The guide 120 includes a channel 130 which extends upward within the guide and into an interior 114 of cup 110. The guide has a first opening 124 and the second opening 126, with the channel 130 continuing between those openings and onward into the interior 134 of a hollow projection 128.

Figure 2:
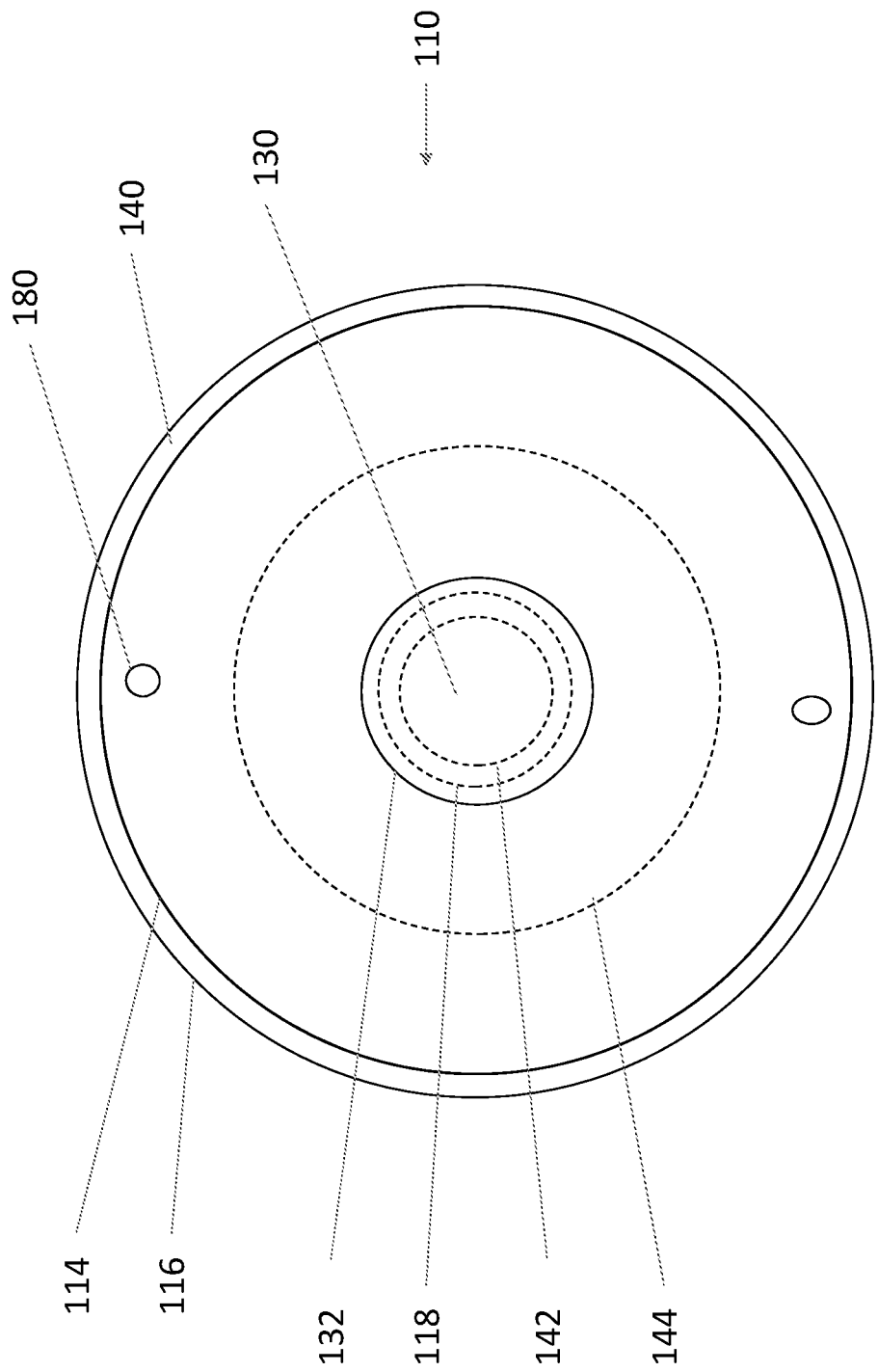
FIG. 2 illustrates a top view of the cup of FIG. 1A.

(FIG. 2 illustrates a diagram of an example of the internal shape of the cup 110 viewing from above.)

In one or more embodiments, exterior 116 of cup 110 comprises an elastic material. For example, quartz fiber, natural rubber, synthetic rubber, nitrile rubber, silicone rubber, urethane rubber, chloroprene rubber, EVA rubber and elastic metals can be used as suitable materials. The principal requirements for the material of the cup are that they be made of a biocompatible material, have a flexibility which permits deformation for introduction into position (see FIG. 3), and a resiliency to seat and form a liquid seal (see FIG. 5A to prevent spillage of bodily fluids during menstruation. The shape of exterior 116 could be V-shaped, U shaped, semicirclular, and so on. The shape of exterior ideally has its biggest diameter at the top 112, so that an open rim 114 seats firmly to tissue to avoid leakage and minimally impedes collection of fluid in the cup 110. In one or more embodiments, exterior 116 is configured to be smooth to make placement and removal more comfortable. Notwithstanding, ribs can be provided between the top 112 and the bottom 118 for reinforcement or other purposes.

In one or more embodiments, open rim 140 is circularly shaped. In another embodiment, open rim 114 is oval shaped. Preferably, the open rim 140 of the cup has an exterior convex shape for rigidity and to firmly seat against human tissue to better avoid leakage. Preferably, the open rim 140, when cup 110 is within the vagina, conforms to the shape of the environment to thereby self-seal to a variety of persons. Optionally, cups can be constructed in small, medium, large or a variety of sizes to accommodate the needs of different individuals.

In one or more embodiments, the cup is made of a single durometer material from inside to outside interior 114 of cup 110 comprises an elastic material. Thus, the interior can comprise any of the materials noted above for the exterior 116. The shape of interior 114 can conform to the exterior shape, or have a different shape, such as due to the presence of the projection 136. In one or more embodiments, the diameter of the interior 114 (in an embodiment in which the interior is circular) near the bottom 118 is larger than diameter of the interior 114 near the top 112. In the illustrated embodiment, the diameter of the interior 114 near the bottom 118 is smaller than diameter of the interior 114 near the top 112.

In one or more embodiments, the interior 114 extends to the open rim 140. The open rim 140 seals in abutting contact with human tissue when the cup 110 is in use. In this construction, the cup 110 better avoids leakage because the interior 114 communicates directly with the open rim 140 to receive blood directly.

In one or more embodiments, the cup 110 preferably includes side holes 180. The side holes 180 better enable the cup to seat firmly against body tissue by permitting any air or fluid trapped between the body tissue and the exterior 116 of the cup 110 to pass through the exterior and into the interior 114. The side holes are preferably near the top 112 of the cup, to assist in establishing a fluid seal between the cup exterior 116 and body tissue (see FIG. 5A).

Optionally, the cup 110 includes a reinforcing rim 138. While one reinforcing rim 138 is illustrated, additional reinforcing rims 138 can be defined in the cup 110, as desired, between the top 112 of the cup and the bottom 118 of the cup. The reinforcement rim 138 can be part of the mold that defines the cup 110 and thus be of the same material, or it can be a co-molded material. As illustrated, the reinforcing rim 138 is positioned near, yet below the holes 180. As noted, the reinforcement rim 138 can be located elsewhere, and additional rims can be provided.

In one or more embodiments, the cup 110 includes a guide 120 at the bottom 118. The guide can be molded together with the cup, but its purpose is not to hold blood, but rather to receive and direct the extractor into position so that the cup and extractor can engage one another to enable the user to remove the menstrual cup for emptying and cleaning. As such, the guide is connected or otherwise extends from the bottom of the cup and has an opposite, free end 122. Both ends of the guide are open to receive the leading end of the extractor 150. There is a first opening 124 which communicates with the bottom of the cup, more specifically, into the opening of the hollow projection 136. There is a second opening 126 at the free end 124 which is where a blunt tip 152 of the extractor 150 is first received. In the illustrated embodiment, the diameter of the guide 120 is smaller than diameter of the open rim 140 because it is provided to assist in safe and secure removal of the cup. As such, the guide, in its largest dimension should be sized smaller than a majority of the exterior 116 of the cup to ensure no detrimental impact on the seal established within the body passageway once inserted. In the illustrated embodiment, the cup and guide together define an overall concave exterior shape which assists in better establishing a seal when positioned within the body.

In one or more embodiments, the guide 120 comprises an elastic material. Thus, the interior can comprise any of the materials noted above for the cup 110. In one or more embodiments, the perimeter of the rim of the guide at second opening 144 is larger than perimeter of the rim of first opening 142, as can be appreciated from FIGS. 1A and 2, to better enable the guide 120 to direct the extractor 150 toward the first opening 124 at the base of the cup 110. In one or more embodiments, the shape of guide 120 can be U-shaped, V-shaped, conically shaped (as illustrated), and so on.

In one or more embodiments, the rim of second opening 144 is convex and rim of first opening 142 is also convex to better ensure atraumatic interaction of the menstrual cup during insertion and removal. In alternative embodiments, these rims can have a different shape, such as rectangular or triangular.

In one or more embodiments, interior of guide 148 has smooth surface to enable the blunt tip 152 of the extractor 150 to slide in an unimpeded manner toward the projection 128 within the cup 110. As described further below, once the blunt tip 152 and helical section 154 have passed into the projection 128, the surface adjacent the tip 152 changes to either a frictional surface or a complementary helical section. Within the projection 128, the interior 134 and the helical section 154 are shaped and sized to permit selective engagement therebetween, as discussed further below. Moreover, the projection is sized such that it extends upward within the interior of the cup 114, but only to a depth which does not reach the top 112 of the cup.

With further regard to the projection 128 of the illustrated embodiment, the channel 130 therein is sized, shaped and made from a material that frictionally engages the helical section of the extractor 154. In another embodiment, the interior 134 of the projection 128 comprises threading 170 which complements the helical section of the extractor 154 to engage the channel 130 in response to rotation of the extractor. In one variation, the threading 170, if provided, terminates before it reaches rim of the first opening 142. In another implementation, threading 170 reaches rim of the first opening 142. This arrangement ensures that the rotation of the extractor and its engagement to the cup 110 is done within a shrouded space which is clear of any body tissue and which, therefore, protects tissue from being pinched or otherwise injured during the removal process.

Referring now to FIG. 1A, the extractor 150 of the illustrated embodiment includes at its leading (distal) end a blunt tip 152 to ensure atraumatic advancement into the vagina in connection with removal of the cup 110. Behind the blunt tip is the distal end of a helical section 154. The helical section 154 is sized and shaped to engage the channel 130 of the projection 128. In one embodiment, it engages frictionally, and in another it engages in a threaded manner, in response to rotation of a handle portion 156 of the extractor. The handle portion can be shaped to minimize interaction with the walls of the vagina. For instance, the handle portion 156 can taper so that its union with the helical section 154 has no step or presents a rounded interface. A base 160 at the proximal end of the extractor 150 has a shape that permits the extractor to be stored in an upright orientation. Optionally, a dent rim 158 defines an ornamental feature between the base 160 and the handle portion 156.

In one or more embodiments, the extractor 150 comprises an elastic material. Thus, the extractor 150 can comprise any of the materials used for the cup 110. In other embodiments, at least portions of the extractor 150 can comprise an inelastic material, such as the handle portion. In one particular embodiment, the extractor is produced in one step within a mold. In another embodiment, the blunt tip 152 and helical portion are produced in a mold while at least the handle portion 156 is made from a different material and thereafter these two components are affixed to one another.

In one or more embodiments, the length of helical section 154 is longer than the length of channel 130 within the projection 128 disposed within the cup. The elastic material of the projection allows it to stretch from an intersection 132 with the bottom 118 of the cup to better ensure that when a user is attaching the helical section within the channel 130, that the projection 128 is not severed to cause a leak or destruction of the cup 110. In another embodiment, the length of helical section 154 is shorter than the length of channel 130. In one or more embodiments, the helical section 154 has an increasing diameter toward the proximal end of the extractor, with a segment having a size that is sufficient to ensure engagement with the channel 130.

In one or more embodiments, the handle portion 156 has an exterior shape to ensure that there is no step or junction which could cause discomfort if it comes into contact with the walls of the vagina. For instance, the exterior can have a cylindrical, convex, concave or tapered shape. In the illustrated embodiment, the handle portion 156 has a smooth surface which tapers to the same general diameter as that of the base of the helical portion 154.

Figure 3:
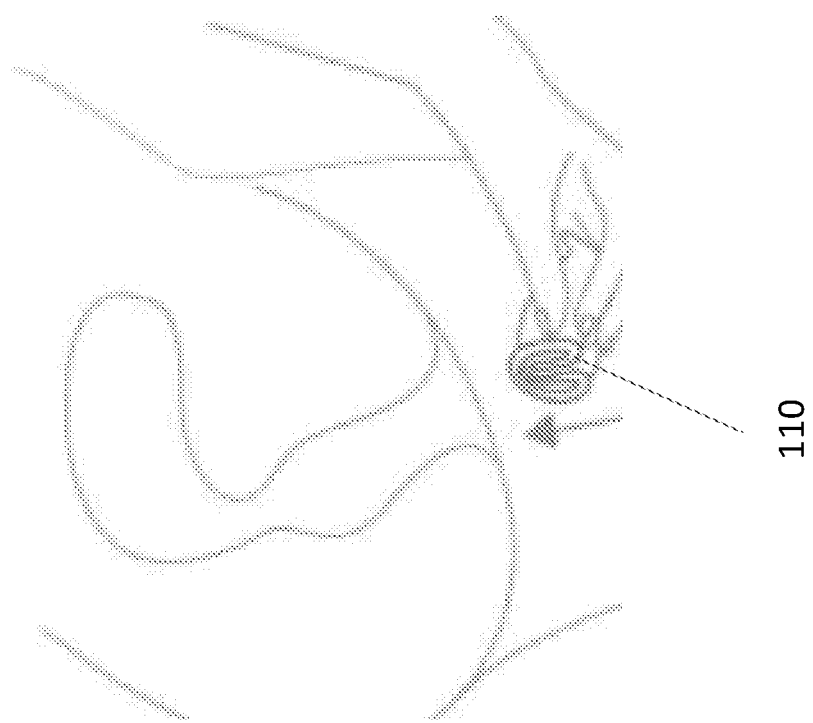
FIG. 3 illustrates a step in the process of inserting the cup of FIG. 1A into a person.

Turning now to FIG. 3, the method of inserting the menstrual cup is illustrated. The elastic top 112 of the cup is deformed as illustrated, such as by pushing one side of the top 112 into contact with the other side and then squeezing or folding the sides in order to reduce the overall size of the cup and reduce the amount of air within. This can be done by grasping the cup 110 firmly between the thumb and the index finger. Then, using a free hand to widen the outer labia, position the cup 110 at the entrance of the vagina and guide it upwards. Once released, the cup 110 will seat itself, automatically, into position, within the vagina.

Figure 4:
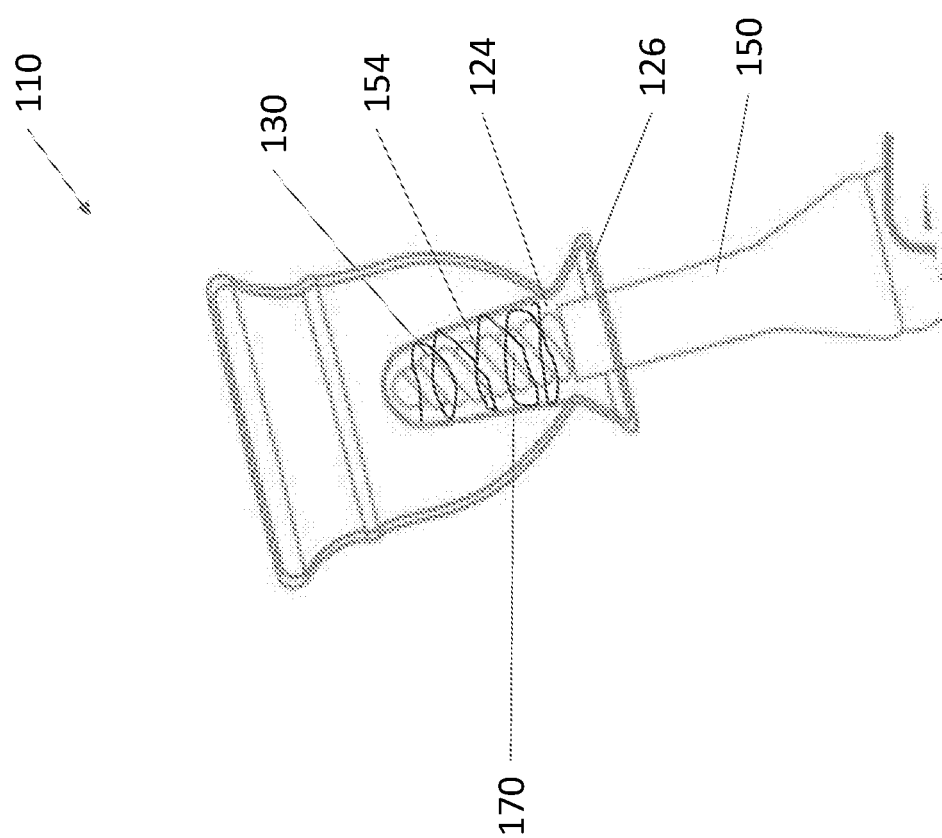
FIG. 4 illustrates a detailed view, showing the cup in section, of the engagement of the cup and the extractor according to the embodiment of FIGS. 1A and 1B.

Referring briefly to FIG. 4, this view illustrates a diagram of how the extractor fits inside the cup. In FIG. 4, the cup is shown as a sectional view, cut down its top center line, while the extractor is shown in side view. The blunt tip 154 is fully received within the channel 130 and the helical portion 154 is engaged to the interior of the hollow projection 128, either by threading 170 (as shown), or by frictional engagement. Regardless of the mechanism relied upon for the engagement between the extractor 150 and the hollow projection 128 of the cup, namely, frictional or threaded, either mechanism utilizes a rotation of the handle portion 156, as described next.

FIG. 5 illustrates the steps taken for removal of the cup 110 from a person using the extractor 150. The user assumes a position that is comfortable for the removal to occur, such as a squat position, a standing position, or a sitting position (e.g., on a toilet).

First, as illustrated in FIG. 5A, the user must insert the extractor 150 into the channel so that it has the configuration shown in FIG. 4. To do this, the user advances the blunt tip 152 of the extractor upward into the vagina and into the guide 120. The blunt tip is advanced and can slide along the interior of the guide to the opening in the bottom 118 of the cup and into the projection 128 (see FIG. 4). Once advanced into the position generally as shown in FIG. 4, the handle is rotated in the direction of arrow A. Rotation of the handle in the direction of arrow A causes frictional, threaded, or both types of engagement, and does so within the confines of the guide 120 and away from sensitive body tissue.

Second, as illustrated in FIG. 5B, after the extractor 150 has been secured inside channel 130, the extractor is wiggled to break a seal between the cup 110 and the walls of the vagina. Thus, for instance, the extractor can be moved leftward and rightward and up and down a bit, as indicated by the various arrows in FIG. 5B.

Third, as illustrated in FIG. 5C, when the user believes that the seal and any suction has been overcome, the cup can be extracted by a pulling motion in the direction of arrow B, 110 by pulling out the extractor 150 as shown.

Thereafter, the contents of the cup can be emptied and the cup rinsed under running water before next use. The cup should be washed regularly in warm water and gentle soap between menstrual cycles, making sure all blood and soap residue are rinsed away to prevent irritation of the vagina. Likewise, the side holes 180 should be cleaned and be free of residue.

It is to be understood that any structural and functional details disclosed herein are not to be interpreted as limiting the systems and methods, but rather are provided as a representative embodiment and/or arrangement for teaching one skilled in the art one or more ways to implement the methods.

It is to be further understood that like numerals in the drawings represent like elements through the several figures, and that not all components and/or steps described and illustrated with reference to the figures are required for all embodiments or arrangements The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing, and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. A menstrual device, comprising:
   a cup having a top, a bottom, a shaped exterior, and an interior;
   an extractor having a blunt tip, a shaped handle, and a helical section extending between the tip and the handle portion;
   a guide attached to the cup and having an opposite, free end, the guide having a first opening into the bottom of the cup and a second opening at the free end; and
   a hollow projection extending within the interior of the cup and having a channel in communication with the first opening and the second opening, wherein the tip is sized and shaped to be received and secured within the hollow projection.

2. The menstrual device of claim 1, wherein the second opening at the free end of the guide is larger than the opening at a first end of the cup in order to facilitate receipt and securement of the tip and helical section within the hollow projection.

3. The menstrual device of claim 1, wherein at least the channel of the hollow projection comprises a material that frictionally engages the helical section of the extractor.

4. The menstrual device of claim 3, wherein the helical section of the extractor frictionally engages the channel in response to rotation of the extractor.

5. The menstrual device of claim 1, wherein at least the channel of the hollow projection further comprises threading for threadedly engaging the helical section of the extractor.

6. The menstrual device of claim 5, wherein the helical section of the extractor threadedly engages the channel in response to rotation of the extractor.

7. The menstrual device of claim 5, wherein the threading is within the hollow projection.

8. The menstrual device of claim 7, wherein the threading terminates before the first opening in the guide.

9. The menstrual device of claim 1, wherein the guide defines a funnel which directs the tip and the helical section into the hollow projection.

10. The menstrual device of claim 9, wherein the funnel has a conical shape.

11. The menstrual device of claim 1, further comprising a plurality of side holes extending between the shaped exterior and the interior.

12. The menstrual device of claim 1, wherein the shaped exterior comprises a cylinder, a convex, a concave, or a tapered exterior.

13. The menstrual device of claim 1, further comprising a reinforcing rim projecting from the shaped exterior at a location between the top and the bottom of the cup.

14. The menstrual device of claim 1, further comprising an open rim disposed at the top of the cup.

15. The menstrual device of claim 1, further comprising a base rim disposed at the bottom of the cup.

16. The menstrual device of claim 1, wherein the handle portion comprises a cylinder, a convex, a concave, or a tapered exterior.

* * * * *